United States Patent
Patil et al.

(10) Patent No.: US 9,226,697 B1
(45) Date of Patent: Jan. 5, 2016

(54) ELECTRONIC SPLINT

(71) Applicants: Sandeep Patil, Menlo Park, CA (US);
Sushmita Roy, Sunnyvale, CA (US)

(72) Inventors: Sandeep Patil, Menlo Park, CA (US);
Sushmita Roy, Sunnyvale, CA (US)

(73) Assignee: SENSIBRACE TECHNOLOGIES, INC., Menlo Park, CA (US)

( * ) Notice: Subject to any disclaimer, the term of this patent is extended or adjusted under 35 U.S.C. 154(b) by 0 days.

(21) Appl. No.: 14/599,971

(22) Filed: Jan. 19, 2015

Related U.S. Application Data

(60) Provisional application No. 62/027,678, filed on Jul. 22, 2014.

(51) Int. Cl.
*A61B 5/11* (2006.01)
*A61B 5/00* (2006.01)

(52) U.S. Cl.
CPC .............. *A61B 5/1121* (2013.01); *A61B 5/1126* (2013.01); *A61B 5/486* (2013.01); *A61B 5/681* (2013.01); *A61B 5/742* (2013.01)

(58) Field of Classification Search
CPC ... A61B 5/1071; A61B 5/4528; A61B 5/1121
See application file for complete search history.

(56) References Cited

U.S. PATENT DOCUMENTS

2002/0024500 A1* 2/2002 Howard ......................... 345/158
2014/0121471 A1* 5/2014 Walker .......................... 600/301

FOREIGN PATENT DOCUMENTS

WO    WO 00/76400 A1 * 12/2000 ............... A61B 5/11

OTHER PUBLICATIONS

Keir et al., "Fingertip loading and carpal tunnel pressure: differences between a pinching and a pressing task" Abstract, J Orthop Res. Jan. 1998, vol. 16, No. 1, pp. 112-115.
Keir et al., "Guidelines for wrist posture based on carpal tunnel pressure thresholds." Abstract, Hum Factors, Feb. 2007, vol. 49, No. 1, pp. 88-99.
Rempel et al., "Effect of Wrist Posture on Carpal Tunnel Pressure while Typing" J Orthop Res. Sep. 2008, vol. 26, No. 9, pp. 1269-1273.
Seradge et al., "In vivo measurement of carpal tunnel pressure in the functioning hand." J Hand Surg Am. Sep. 1995, vol. 20, No. 5, pp. 855-859.
Weiss et al., "Positioning of the wrist associated with the lowest carpal-tunnel pressure: implications for splint design." J Bone Joint Surg Am, Nov. 1995, vol. 77, No. 11, pp. 1695-1699.
Werner et al., "Intracarpal canal pressures: the role of finger, hand, wrist and forearm position" Clinical Biomechanics, 1997, vol. 12, No. 1, pp. 44-51.
Werner et al., "Carpal tunnel syndrome: pathophysiology and clinical neurophysiology" Clinical Neurophysiology, May 21, 2002, vol. 113, pp. 1373-1381.

* cited by examiner

*Primary Examiner* — Unsu Jung
*Assistant Examiner* — Joseph M Santos Rodriguez
(74) *Attorney, Agent, or Firm* — Knobbe Martens Olson & Bear LLP

(57) ABSTRACT

A monitoring device mounted to a user can be used to estimate a position or orientation of a body portion of the user, such as a joint or jointed portion of the user. Radiation can be emitted toward the body portion and a reflection of this radiation can be received. The reflected radiation can then be used to estimate a position of the body portion of the user.

14 Claims, 11 Drawing Sheets

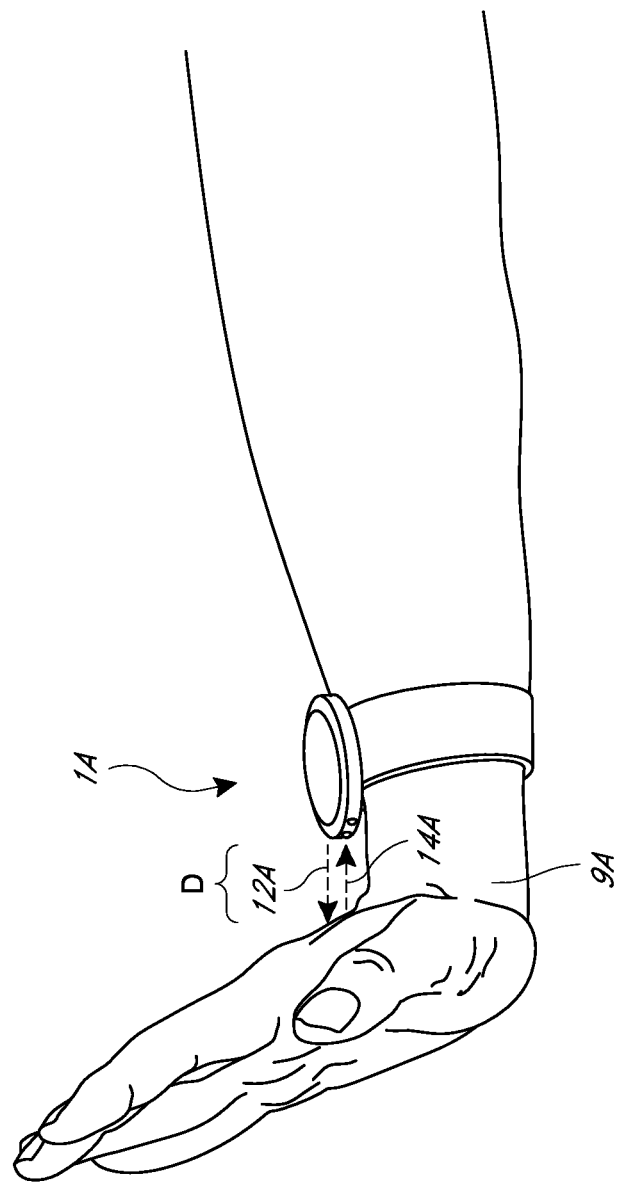

ELECTRONIC SPLINT

BACKGROUND

1. Field

The application relates to wearable electronic monitoring devices such as electronic splints and braces.

2. Description of the Related Art

Injuries related to repetitive or continuous musculo-skeletal movements and positioning have taken on a growing level of significance in recent years. Excessive computer (keyboard and mouse) and smartphone use has become more frequent and widespread and this together with poor wrist mechanics may contribute to conditions such as Carpal tunnel syndrome (CTS).

Current treatments for these injuries include anti-inflammatory drugs which treat the symptoms instead of the underlying problems. Exercises to treat or prevent these injuries can be helpful, but require additional effort and can be limited in their effects. Physical braces and splints can prevent the movements and positions that cause these injuries and can prevent further injuries, but they also restrict movement, do not teach better wrist mechanics, and are not always aesthetically pleasing. Thus, there is a need for improved methods for preventing and treating these injuries.

Further, there is a need for improved methods for monitoring, correcting, or measuring musculo-skeletal movements. In addition to injury concerns, the position of various joints may be relevant to athletic performance or other goals. Thus, devices that are substantially non-intrusive are desired.

The methods and apparatuses described herein can be directed toward one or more of these goals, or other goals that will be apparent from the description herein.

SUMMARY

In one embodiment, a monitoring device for monitoring a wrist of a user includes a wrist strap and a main body. The wrist strap can be configured to mount to a user's wrist. The main body can be attached to the wrist strap and can include an emitter, sensor, feedback module, and processing module. The emitter can be configured to emit radiation toward a dorsal side of the user's wrist when the monitoring device is worn by the user. The sensor can be configured to receive the radiation emitted by the emitter and reflected by the user's wrist at least when the user's wrist is in extension, and to output a signal in response to said received radiation. The feedback module can be configured to provide immediate feedback to a user. The processing module can be configured to receive said signal and to control the feedback module to provide immediate feedback according to a degree of extension of the user's wrist as indicated by the signal.

In a further embodiment, a method of preventing and/or treating wrist and hand injury can be provided. Radiation can be emitted toward a wrist of a user, and reflected radiation can be received from the wrist of the user. A degree of extension of the wrist can be estimated according to the intensity of the reflected radiation received from the wrist of the user. Feedback can then be provided according to the estimated degree of extension.

In a further embodiment, a monitoring device for monitoring a body portion of a user can include a mounting element, an emitter, a sensor, a feedback module, and a processing module. The mounting element can be configured to allow the monitoring device to be mounted to a user. The emitter can be attached to the mounting element and configured to emit radiation toward a body portion of the user. The sensor can be attached to the mounting element and configured to receive radiation emitted from the emitter toward the body portion and reflected by the body portion toward the sensor, and to output a signal in response to said received radiation. The feedback module can be configured to provide feedback to a user. The processing module can be configured to receive the signal from the sensor and to instruct the feedback module to provide feedback to the user indicative of a position of the body portion as indicated by the signal from the sensor.

In a further embodiment, a method of monitoring a body portion of a user and providing feedback to the user can be provided. Radiation can be emitted toward a body portion of a user, and radiation reflected from the body portion of the user can be received. A position of the body portion relative to another body portion of the user can be estimated according to the reflected radiation received. Feedback can then be provided to the user according to the estimated position of the body portion of the user.

BRIEF DESCRIPTION OF THE DRAWINGS

Further objects, features and advantages will become apparent from the following detailed description taken in conjunction with the accompanying figures showing illustrative embodiments, in which:

FIG. 3C depicts the monitoring device of FIG. 1A being worn by a user in a dorsal position, with a joint in an extremely-strained position.

DETAILED DESCRIPTION OF CERTAIN PREFERRED EMBODIMENTS

Figure 1A:
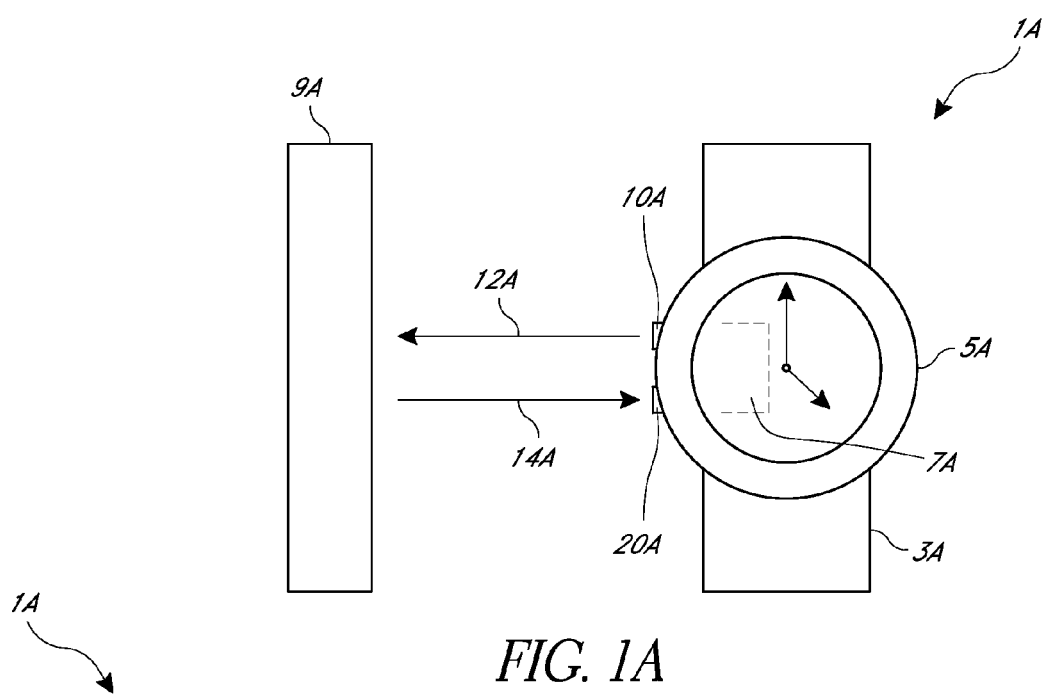
FIG. 1A depicts a perspective view of a monitoring device embodiment in the form of a watch.

As described herein, a variety of devices can be used to measure the physical position of a jointed portion of a user. For example, the physical position of a user's wrist can be measured using a distance-measuring system using infrared energy. The infrared system can include an emitter and a sensor located such that infrared energy can be emitted toward a body portion of a user, and the reflected energy (specularly reflected, back-scattered, or other types) can be received by the sensor. The amount or intensity of reflected energy received by the sensor can indicate a distance from the emitter to the body portion and back to the sensor. This distance can then be used to estimate body positions such as an angle of a jointed limb or body extremity, as the angle of the joint will affect a distance between two portions of a user's body. Numerous variations on this principle of measurement are possible.

For example, in some embodiments, other forms of energy can be used. Electromagnetic radiation can be used outside the infrared spectrum, such as visible light, UV radiation, microwave radiation, and X-ray radiation. In other embodiments non-electromagnetic radiation can be used, such as sound waves using ultrasound sensors and measured electrical characteristics using capacitive sensors, to estimate a distance between points on a user's body.

In further embodiments, distance can be measured without purposefully emitting radiation. For example, using ambient light, an imaging device can recognize a portion of the user's body and estimate its position or distance based on characteristics such as its position, size, orientation, or other characteristics derived from a captured image. In other embodiments, the distance can be estimated based on infrared radiation naturally emitted from a user's body based on body heat, with higher intensities being associated with, for example, a smaller distance from the body portion. In such embodiments, a temperature sensor might also be included to measure a user's body temperature, which can relate to the intensity of infrared radiation emitted by the body.

In further embodiments, distance can be measured indirectly. Alternatively, other characteristics about a user and/or a user's body position can be measured using various sensors. For example, accelerometers, gyroscopes, magnetometers, strain sensors, angular encoders, linear encoders, and other position/force sensors can be used to measure a user's body orientation relative to itself or gravity. Further, in some embodiments sensors can measure physiological characteristics such as blood pressure, heart rate, blood oxygen concentration, or use myoelectric sensors to estimate various characteristics about the user.

Although the embodiments described herein will focus on measurements of distance using infrared sensors, other sensors can optionally also be used instead of the described infrared sensors, or in combination with such sensors. Thus, for example, the infrared sensors described herein can be combined with a gyroscope to measure a joint's angle with respect to itself (such as, in flexion or extension) and also measure the joint's angle relative to Earth's gravitational and/or magnetic fields (such as with an accelerometer and/or magnetometer).

Figure 1B:
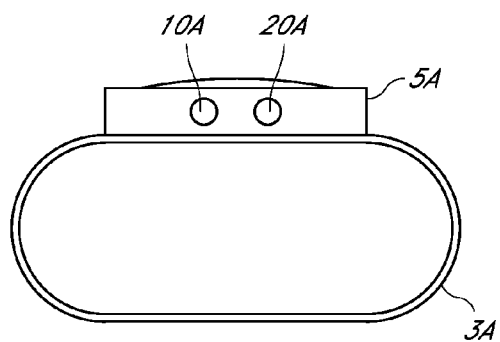
FIG. 1B depicts a side view of the monitoring device of FIG. 1A.
Figure 1C:
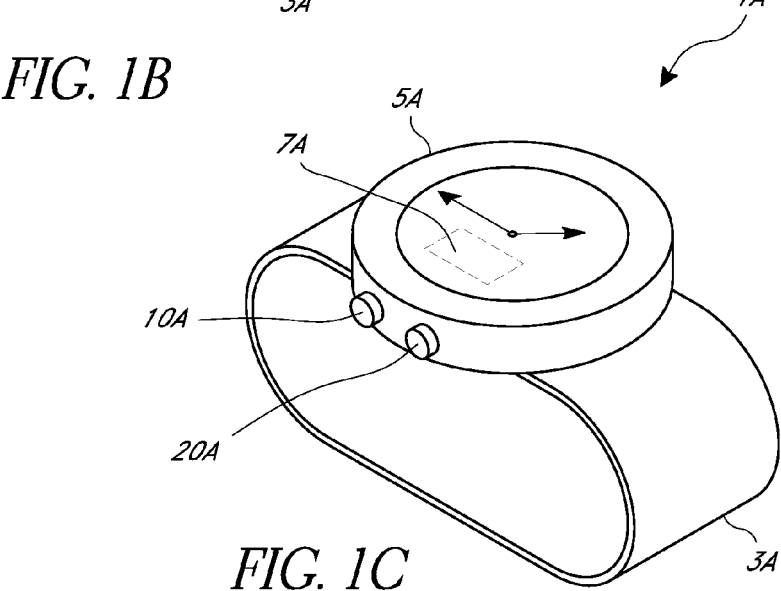
FIG. 1C depicts a top view of the monitoring device of FIG. 1A.

FIGS. 1A-1C depict an embodiment of a monitoring device 1A in the form of a wrist watch. The wrist watch can include a strap 3A and a main body 5A, the strap 3A providing a mounting element that is configured to allow the watch to be mounted to a user. In other embodiments, other types of mounting elements can be used such as a clip, ring (metal, elastic, fabric, or otherwise), adhesive, article of clothing, or other means for attachment to a user. Although not depicted, the watch 1A can include standard watch features such as a latch for adjusting the size of the watch and other features that may be desirable for wearing by a user.

The main body 5A of the watch 1A can include a display 7A that can indicate information such as a time, but also additional information related to the physical position of a portion of a user, as further described herein. Within the main body 5A, the watch 1A can include various electronic modules, further described herein, for operating the monitoring elements of the watch 1A, processing data received, communicating with a user or other devices, and performing other desirable functions.

On an exterior portion of the main body 5A, an emitter 10A and a sensor 20A (such as an infrared emitter and sensor) are depicted. Both the emitter 10A and the sensor 20A can be positioned, as shown, to be directed toward the same body portion of a user, such as a dorsal side of the user's wrist/hand region. More particularly, the emitter and sensor can be positioned to measure wrist extension (upward or dorsal bending at the wrist). However, in other embodiments they can be directed toward other body portions of a user instead of or in addition to the dorsal side of the user's wrist/hand region to measure wrist extension.

The emitter 10A can be, for example, a laser, light emitting diode, a laser diode, a collimated incandescent lamp or another device capable of emitting radiation. The sensor 20A can be chosen to match the emitter 10A. For example, where the emitter 10A emits electromagnetic radiation such as infrared radiation, the sensor 20A can be a photosensor such as a photodiode. It could also be an integrated sensing system that incorporates: multiple photodiodes, an analog-to-digital converter, a signal processor, a plurality of LED based emitter drivers and a digital control interface, in a surface mountable miniature integrated circuit package, such as Silicon Laboratory's Si114x series.

Figure 2A:
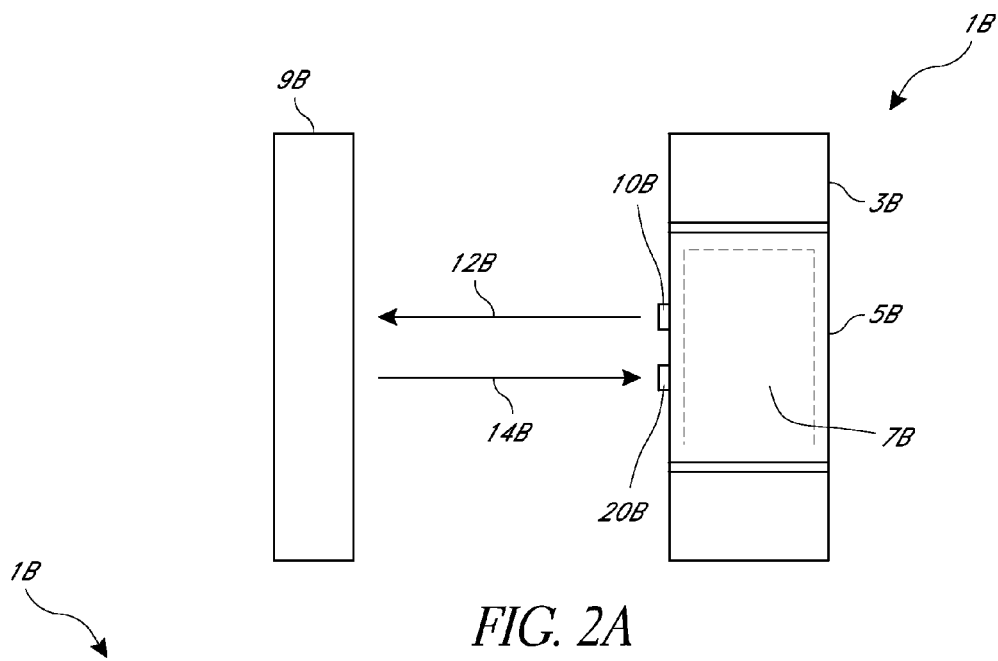
FIG. 2A depicts a perspective view of a monitoring device embodiment in the form of a fitness band.
Figure 2B:
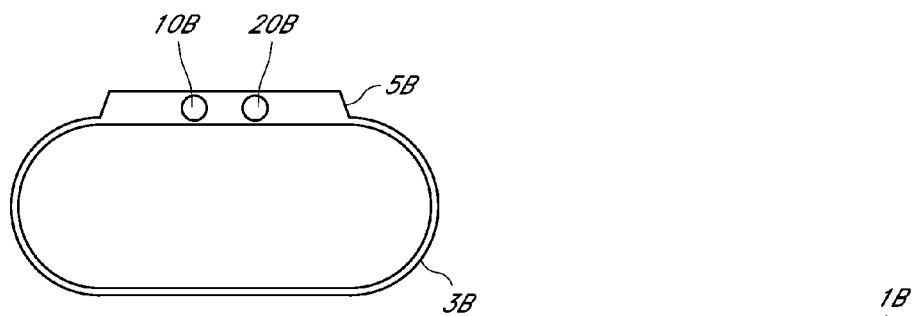
FIG. 2B depicts a side view of the monitoring device of FIG. 2A.
Figure 2C:
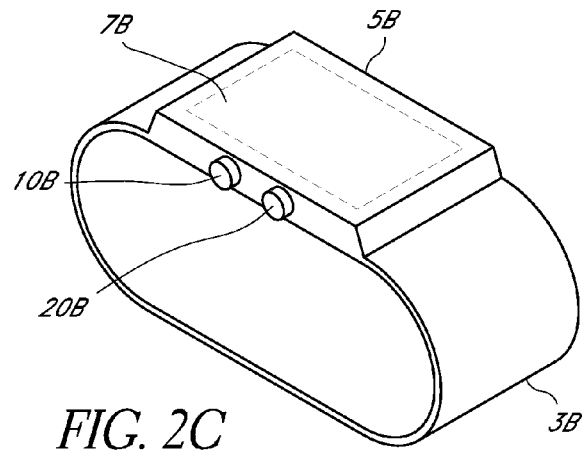
FIG. 2C depicts a top view of the monitoring device of FIG. 2A.

Many of the features and functionalities described herein are not specific to a watch. Thus, in some embodiments a monitoring device can be in the form of, for example, a wrist band 1B as depicted in FIGS. 2A-2C. The band can include a strap 3B, main body 5B, emitter 10B, sensor 20B, and other features similar to the wrist watch 1A, other than the watch-specific features. It will be understood that corresponding reference numbers on either of the watch 1A or band 1B can have similar characteristics. Thus, for example, the strap 3A can be similar to the strap 3B, and further variations on the strap 3A described herein (such as a clip, ring (metal, elastic, fabric, or otherwise), adhesive, article of clothing, or other means for attachment to a user) can also be applied to the strap 3B. Similarly, references to, for example, a "strap 3" can be understood to apply to either of straps 3A, 3B, or other straps described herein.

FIGS. 1A and 2A schematically depict measurement of a user's body position using the monitoring devices 1A, 1B. As shown, the emitter 10 emits outgoing radiation 12 toward a monitored body portion 9. The monitored body portion 9 can then reflect this outgoing radiation 12 to create reflected incoming radiation 14 that is received by the sensor 20. Although the radiation emitted by the emitter 10 and reflected by the sensor 20 is depicted as a narrow beam, it will be understood that the radiation need not be substantially narrow or spatially concentrated. For example, in some embodiments the emitter can be directional, such as with a laser or an LED with focusing optics. In other embodiments, the emitter can be less directional, providing a broader cone of light or other radiation dispersal pattern toward the monitored body portion 9. In such embodiments, the cone of radiation can be concentrated within an acute angle with its apex situated on the emitter.

Similarly, the sensor 20 can optionally be configured to receive radiation from a broad range of directions, or from only a specific direction. The angular span of the sensor 20 can be limited, for example, with optics or other features.

Generally, the emitter 10 and sensor 20 can be configured such that a substantial portion of the radiation from the emitter 10 can be reflected by the monitored body portion 9 (at least when in a position to be detected) and a substantial portion of that reflected radiation can be detected by the sensor 20, such that the position of the body portion can be determined. As discussed above, this position can be determined by the amount or intensity of reflected radiation received by the sensor 20, but other mechanisms can also be used.

Further, in some embodiments multiple emitters 10A can be paired with a single sensor. The two emitters 10A can be offset from each other by a certain distance and each provide cone-shaped emitted radiation. The emitters 10A can be configured such that their cone-shaped radiation patterns overlap in a region of interest of body portion 9, such that the radiation reflected from that region can be particularly high. In this way, the emitters 10A and sensor 20A can selectively focus on the region of interest of body portion 9, resulting in a significantly stronger response from that region relative to others.

Figure 3A:
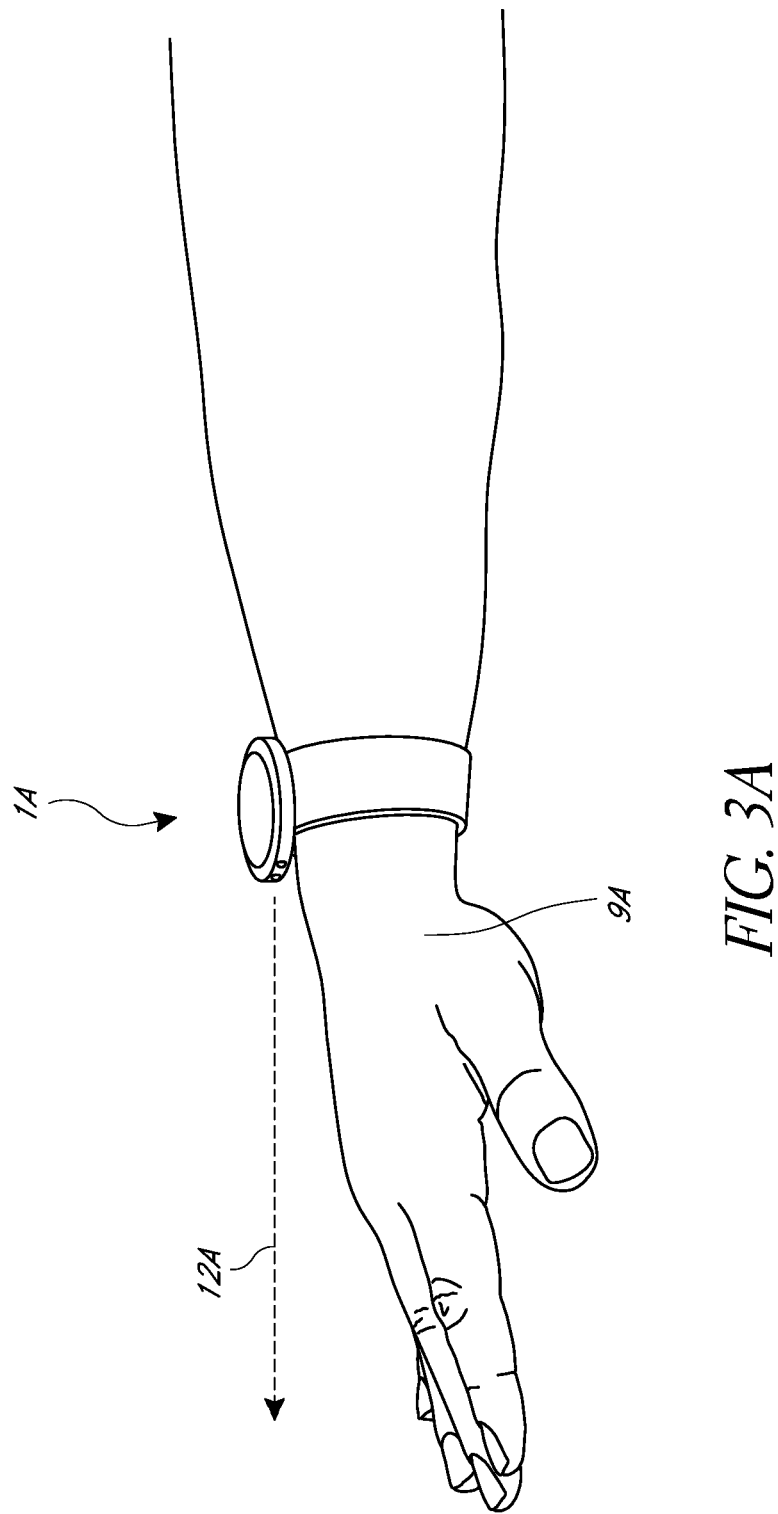
FIG. 3A depicts the monitoring device of FIG. 1A being worn by a user in a dorsal position, with a joint in a neutral position.
Figure 3B:
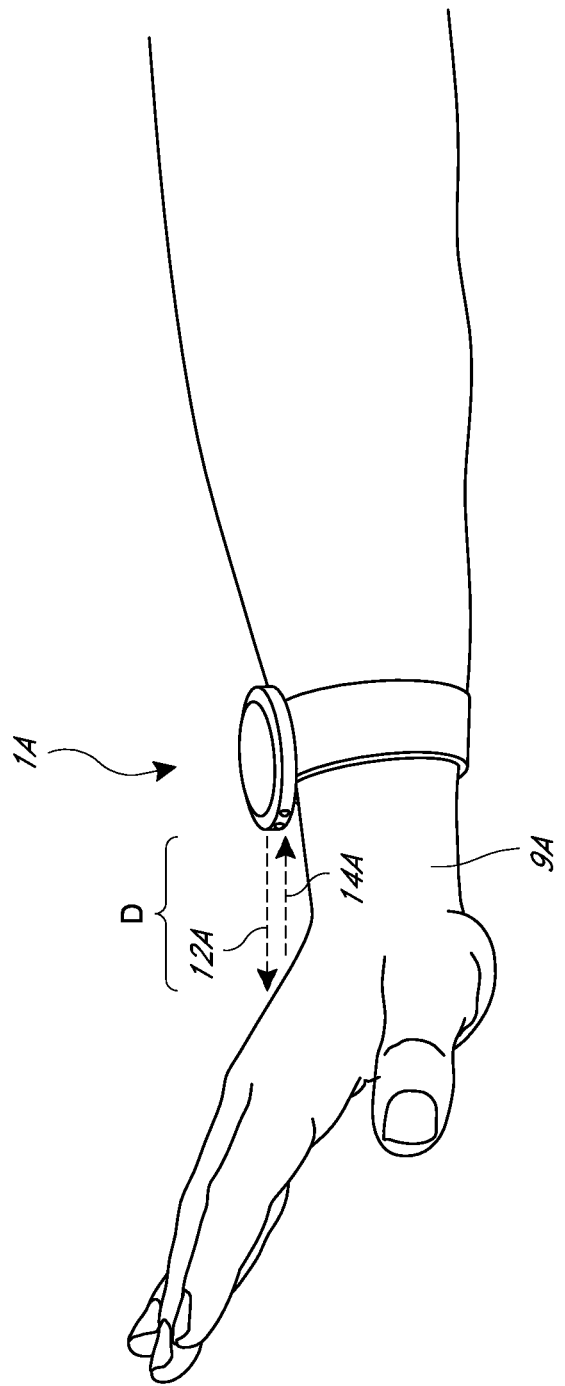
FIG. 3B depicts the monitoring device of FIG. 1A being worn by a user in a dorsal position, with a joint in a moderately-strained position.

FIGS. 3A-3C depict this concept in the context of the wrist watch monitoring device 1A, measuring wrist extension. The monitoring device 1A is worn in a posterior or dorsal position, with the emitter 10A and sensor 20A oriented toward the monitored body portion 9A (the wrist). As shown, the emitter 10A can emit outgoing radiation 12A toward the wrist 9A in a direction substantially parallel with the forearm. In FIG. 3A, the wrist joint is depicted in a neutral position. Thus, the outgoing radiation 12A (in a direction parallel to the forearm) is not reflected by the user's body and proceeds out to the ambient environment. As a result, the sensor 20 does not receive reflected radiation, and thus reports a low amount or intensity of reflected radiation. However, as noted above, in some embodiments the emitter 10A can emit a broader cone of radiation, and this cone might be broad enough to contact the user's body, even when in the position depicted in FIG. 3A. Nevertheless, the amount of reflected radiation received by the sensor 20A can be small in a way sufficiently repeatable to be identified by the monitoring device 1A.

In FIG. 3B, the wrist 9A is in moderate extension. In this position, as shown, the outgoing radiation 12A can contact the user's hand and a resulting reflected radiation 14A can be received by the sensor 20A. The intensity of radiation detected by the sensor 20A can indicate a distance D between the emitter/sensor and the body portion, and that distance can indicate an angle of bending at the wrist. Thus, for example, a stronger intensity measured by the sensor indicates a higher angle of wrist extension. Because of the physical principles governing propagating radiation, and also because the outgoing radiation 12A can be slightly dispersing (for example, as a cone), the intensity of the radiation can decline with distance, such that a lower intensity indicates a longer distance. As further discussed herein, the intensity of the radiation can thus be used to estimate the angle of the wrist.

In FIG. 3C, the wrist 9A is in extreme extension. In this position, as shown, and similar to FIG. 3B, the outgoing radiation 12A can contact the user's hand and a resulting reflected radiation 14A can be received by the sensor 20A to indicate a distance D. Of particular relevance when compared to FIG. 3B, the distance D is now shorter, resulting in a higher intensity measured by the sensor 20A.

The monitoring device 1A can use the data from the sensor 20A to estimate an angle of the wrist. As described above, this angle can be estimated according to the intensity of radiation received by the sensor 20A. Upon receiving this radiation, the sensor 20A can output a signal to one or more processing modules, that can be located on the monitoring device 1A, or on an auxiliary device that can be in communication with the monitoring device 1A. For example, in some embodiments the monitoring device 1A can communicate continuously or at discreet times with auxiliary devices such as a user's phone, a computer, a server (through a wired or wireless network), or other devices. In some embodiments, the monitoring device 1A can include a cable or an electric connector configured to connect to a cable that can provide a data connection to an auxiliary device. In further embodiments, the monitoring device 1A can include a wireless communications module capable of communication over Bluetooth, wireless Wi-Fi, ANT, or other wireless communication protocols.

Although processing steps described herein may be performed on a module on the monitoring device 1A, in other embodiments they may be performed on auxiliary devices in communication with the monitoring device. Further, the step of communicating with the auxiliary device may be performed at a variety of times, such that data output from the sensor 20A may be pre-processed or temporarily stored in a data storage device (such as a solid state data storage device) on the monitoring device 1A prior to transmission to the auxiliary device.

The angle implied by the data output from the sensor 20A can be translated into an estimated angle using a variety of methods. For example, a table or graph indicating an expected relationship between the output (indicative of the intensity) and the angle can be used. In further embodiments, one or more equations can be used to indicate the relationship. Further, in some embodiments additional variables can be used to determine the estimated angle. For example, in some embodiments the monitoring device 1A can be calibrated for each individual user, as they might have different hand/wrist sizes, leading to different distances for each angle, or different flexibilities leading to different levels of concern for a given angle. Thus, prior to use a user can move the measured body portion through a series of angles known to the device during a predefined, short period of time, such that the device can associate those known positions with coinciding measurements by the sensor 20A during the short period of time. The monitoring device 1A can also optionally include additional sensors, such as those discussed herein, that can provide additional data indicative of a position of a user's wrist joint, or other portions of a user's body.

The estimated angle, or other position, of the user's wrist, or other body portion, can then be used to provide an appropriate feedback to the user. In some embodiments, the monitoring device 1A can provide immediate feedback to the user. For example, the monitoring device (or an auxiliary device carried by the user such as a phone) can include a feedback module to provide visual, auditory, or haptic feedback to the user. In some embodiments, the monitoring device may include one or more visible feedback modules such as LEDs that can emit visible light when the monitored body portion is in an undesirable position. As a specific example, a substantially desirable or neutral wrist position (for example, less than approximately 20 degrees) such as that shown in FIG. 3A may cause a green light to be provided. If a moderately undesirable position (for example, between approximately 20 and 60 degrees from neutral wrist position) such as that shown in FIG. 3B is reached, a yellow light can be provided. Finally, if a severely undesirable position (for example, greater than approximately 60 degrees from neutral wrist position) such as that shown in FIG. 3C is reached, a red light can be provided. In further embodiments, similar information can be provided on a visual display such as an LCD on the monitoring device (such as display 7A, as depicted in FIGS.

1A, 1C). The display can also provide more complex feedback, such as a length of time spent in an undesirable position, a more precise position of the monitored body portion, or other data. Similar audio feedback can be provided, for example, if the monitoring device or the auxiliary device includes a speaker, and similar haptic feedback can be provided with a vibrator. Further, the specific angles considered desirable or undesirable can be adjusted to fit the varying medical needs of different users. Even further, the specific angles considered desirable or undesirable can be adjusted to fit other needs of individual users. The ranges described herein are provided merely as examples.

Further, in some embodiments, this feedback can be provided immediately, upon the monitoring device 1A recognizing the position. It can also optionally be delayed. For example, in some embodiments the feedback can be provided after the body portion is in an undesirable position for a predetermined extended period of time (such as 1 minute, 5 minutes, 10 minutes, or more than 10 minutes). Further, in some embodiments the feedback can be sustained, or repeated while the position is maintained.

The monitoring device 1A can also optionally store data to be provided to a user at a later time. For example, the data can be stored on the monitoring device 1A or be transmitted to an auxiliary device that can also store the data. The data can then be provided to a user in a variety of formats, such as in a graph, table, or a report indicating a cumulative level of stress, strain, or other conditions put on the body portion being monitored. This data can be viewed on a web page, in an app, in an email sent to the user, or other media. Similarly, this data can be provided to a third party, for example, at the option of the user.

Further, in some embodiments the data measured by the monitoring device 1A can be used to determine the measurement behavior of the monitoring device. In some embodiments, the monitoring device 1A can measure continuously or at regular intervals. However, in other embodiments the frequency of measurements by the monitoring device 1A can be determined by the movements or position of the user. For example, in some embodiments the device 1A can take measurements at a higher frequency for as long as an undesirable position is detected. In further embodiments, the monitoring device 1A can include an accelerometer or other sensor configured to measure sudden movements. Such sudden movements can then cause the monitoring device 1A to make one or more measurements of the body portion to determine to what position it may have moved. In further embodiments, the frequency of measurement can be affected by other data, such as a reduction in blood flow, change in body temperature, or other physical or physiological changes that may indicate increased stress or an undesirable position.

Additionally, in some embodiments the relationship between sensor 20A output and the estimated angle of the body portion can vary over time. For example, in some embodiments the sensor 20A can be recalibrated during use. As discussed regarding FIG. 3A, if the wrist joint is in a neutral position then the sensor 20A should receive no reflected radiation. However, if the device is being used in an environment with numerous strongly reflecting surfaces or other sources of radiation, the angle might be miscalculated. Thus, in some embodiments it may be desirable to recalibrate the sensor 20A output corresponding to a neutral position, for example, by determining the lowest sensor measurement over a long time period (such as longer than 10 minutes, 20 minutes, or 30 minutes). Recalibration for maximum bend can be done in a similar manner, determining the highest sensor measurement. Further, in some embodiments the monitoring device 1A can receive a command from the user to recalibrate, after which the user can move the body portion monitored through its full range of motion in a limited amount of time, such that a new high and low measurement can be determined.

Figure 4:
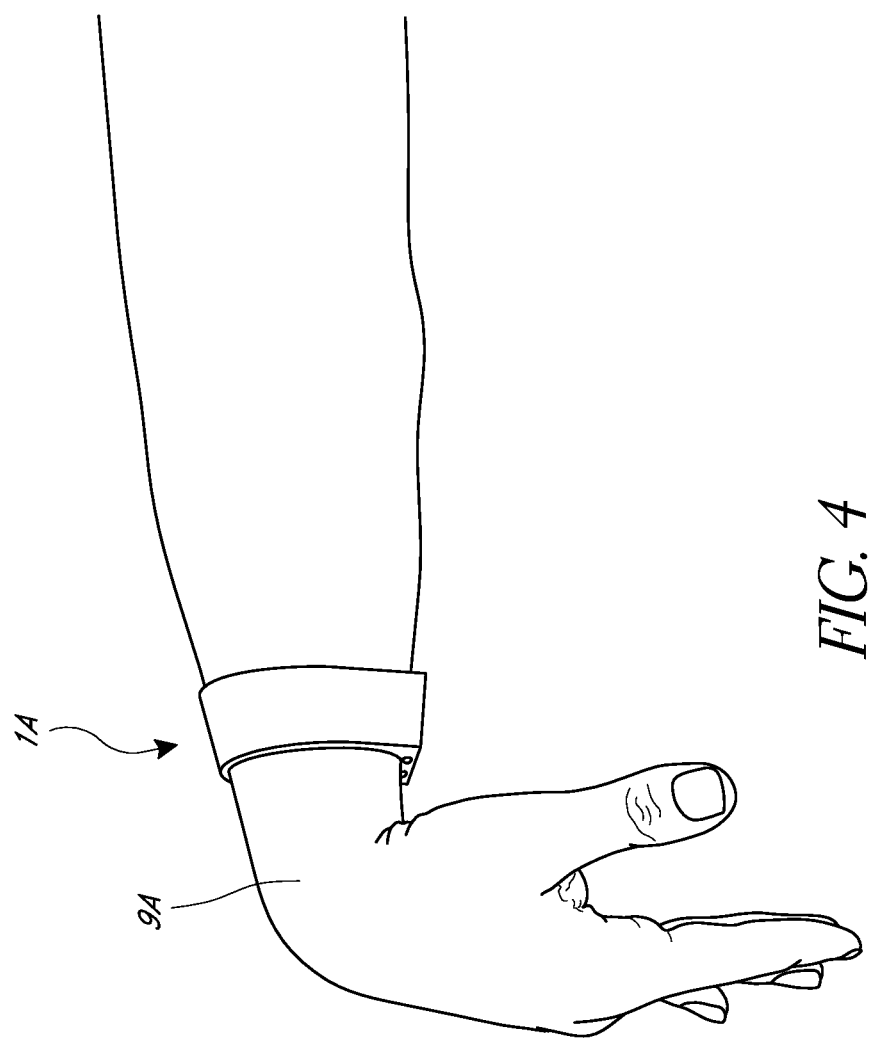
FIG. 4 depicts the monitoring device of FIG. 2A being worn by a user in a palmar position, with a joint in a moderately-strained position.

Similar processing techniques can be used for other monitoring devices that measure other body portions. For example, these processing techniques can also be used with the monitoring device 1B as depicted in FIG. 4. FIG. 4 is analogous to FIG. 3B, but with the monitoring device 1B as a band, and the device measuring the palmar side of the wrist joint 9A. Thus, the monitoring device 1B can measure wrist flexion in the same way that the monitoring device 1A in FIGS. 3A-3C can measure wrist extension.

Figure 7:
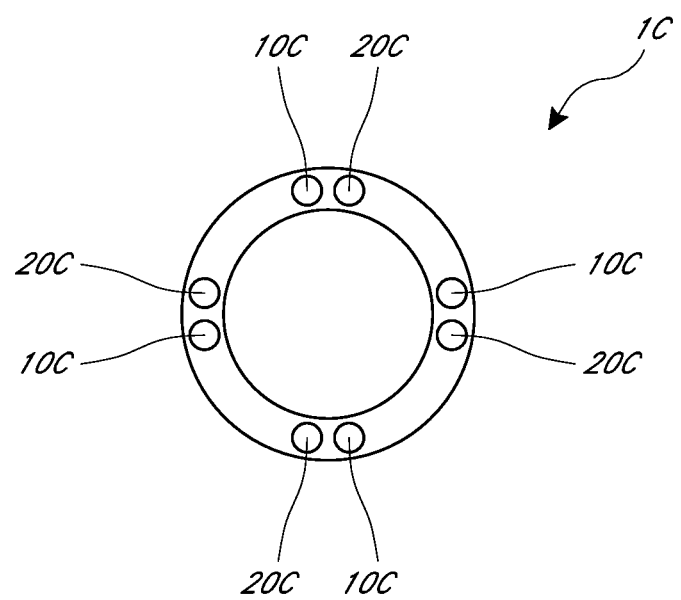
FIG. 7 depicts a monitoring device embodiment with multiple emitter and sensor pairs.

Similarly, in some embodiments the monitoring device 1C can include more than one pair of emitters 10C and sensors 20C, as depicted in FIG. 7. As shown, the device can include 4 pairs of emitters 10C and sensors 20C. Thus, the device 1C can measure wrist extension, flexion, and radial/ulnar deviation, in ways similar to those described above. Notably, such a device can aid in calibration. For example, if wrist extension is detected, no reflected energy should be provided to the palmar sensors on the device 1C, so the low measurement for the corresponding sensor 20C can be recalibrated. The same can be done for the dorsal sensors when wrist flexion is detected. The monitoring device 1C in FIG. 7, which includes sensors and emitters on 4 sides, can be particularly useful for joints that allow for rotation in two directions, such as the wrist, shoulder, hip, ankle, neck, and back.

Figure 5A:
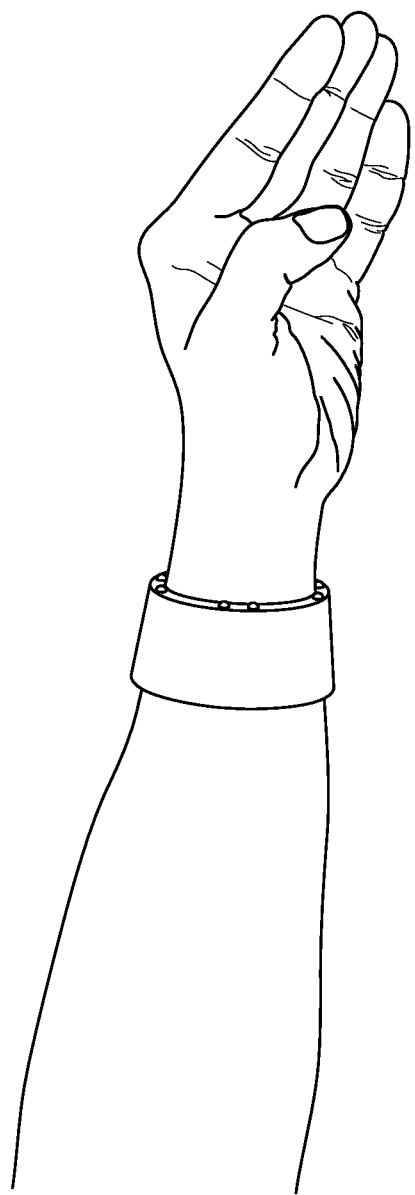
FIG. 5A depicts a monitoring device embodiment mounted to a user with a thumb in a bent position.
Figure 5B:
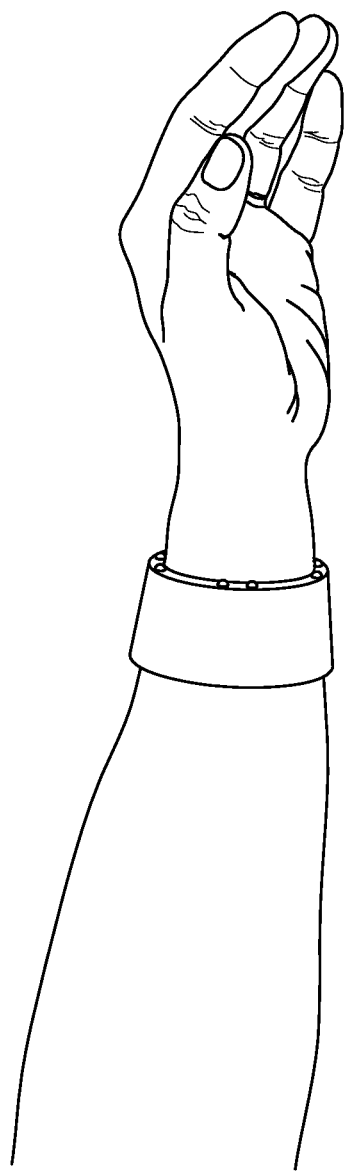
FIG. 5B depicts the monitoring device embodiment of FIG. 6A mounted to a user with a thumb in a neutral position.

The monitoring device 1C can also potentially measure movements of the thumb, as depicted in FIGS. 5A, 5B. Notably, the thumb can protrude from a side of the wrist, and thus be identified by a sensor 20C on a side of the wrist corresponding to the thumb. Further, movements of the thumb outward (abduction) can increase reflectance from the thumb's surface to the sensor 20C, such that this motion can be detected. Similarly, a movement of the thumb towards the palm (adduction), as shown in FIG. 5A relative to FIG. 5B, can cause the thumb to no longer be detected by the sensor 20C on the side, but start being detected by the palmar sensor. Thus, particular combinations of changes in the intensity measured by each sensor 20C can indicate a position of the thumb.

Figure 6A:
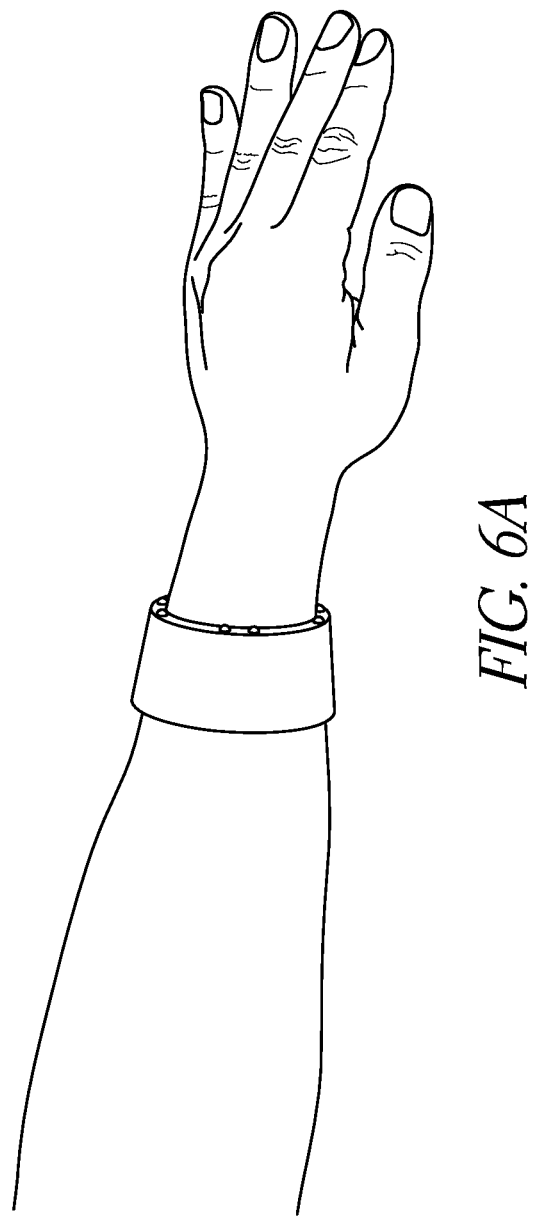
FIG. 6A depicts a monitoring device embodiment mounted to a user with a wrist in a rolled position.
Figure 6B:
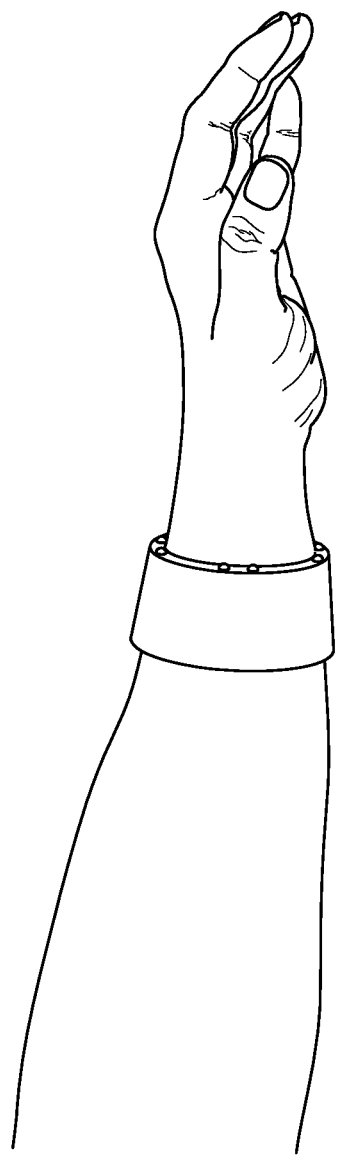
FIG. 6B depicts the monitoring device embodiment of FIG. 6A mounted to a user with a wrist in a neutral position.

The monitoring device 1C can also potentially measure rotations of the wrist in a rolling motion (pronation and supination), as shown in FIGS. 6A, 6B. The medial/lateral sides of the wrist tend to protrude outwardly, such that they would provide a reflectance to corresponding medial/lateral sensors 20C. However, if the wrist is rolled around the axis of the forearm, the medial/lateral sides of the wrist could begin to align with the dorsal/palmar sensors 20C, such that they would receive a reflected energy simultaneously. Notably, both the dorsal and palmar sensors 20C would not receive a reflectance simultaneously during flexion or extension. Thus, a rolling motion of the wrist can also be detected.

In further embodiments, various motions of the wrist joint can be detected using additional emitters, sensors, and reflecting objects. For example, in some embodiments a ring can be used in combination with a wrist watch or band. In some embodiments, the ring can include an emitter and/or sensor that can pair with a corresponding sensor and/or emitter on the wrist watch or band. In other embodiments, the ring can include highly reflective material, such that its orientation relative to an emitter and sensor on the wrist watch or band can cause large changes in reflected radiation detected by the sensor. Thus, a variety of positions and motions can be detected.

Further, in some embodiments monitoring devices such as those described herein can be provided on other parts of the body, or using other types of wearable sensors. For example, in the context of a wrist, similar sensors can also be provided on a bracelet, glove, or other wearable item. Further, wearable items can include sensors at other joints. For example, similar sensors can be provided on an arm band to measure an elbow or shoulder joint; a headband to measure a position of the neck; a waist band, belt, or shirt to measure a position of the back; a belt, leg band, shorts, or pants to measure a position of the hip joint; a leg band, shorts, or pants to measure a position of the knee joint; or a leg band, shoe, or sock to measure a position of the ankle joint.

In some embodiments, these devices can be used to monitor behavior. For example, as described above, many wrist injuries can be treated or prevented by preventing or reducing extensions and flexion of the wrist to reduce stress on the wrist. This can be facilitated by indicating to a user when they are entering and/or holding these positions. Similar treatments can also be provided to other parts of the body. Further, the monitoring can be useful in non-medical contexts. For example, in sports or other performance-dependent activities, it may be desirable to keep particular body portions in certain positions (for example, keeping a joint straight or at a desired angle during a golf swing, basketball shot, pitching motion, etc.). The devices described herein can estimate a position or angle of a particular body portion or joint over time, and provide immediate or delayed feedback to a user about their position or motion at critical times during use. Thus, the user can learn to maintain the desired position or motion during these activities.

Unless the context clearly requires otherwise, throughout the description and the claims, the words "comprise," "comprising," "include," "including," and the like are to be construed in an inclusive sense, as opposed to an exclusive or exhaustive sense; that is to say, in the sense of "including, but not limited to." Additionally, the words "herein," "above," "below," and words of similar import, when used in this application, shall refer to this application as a whole and not to any particular portions of this application. Where the context permits, words in the Detailed Description using the singular or plural number may also include the plural or singular number, respectively. The words "or" in reference to a list of two or more items, is intended to cover all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language does not imply that features, elements and/or states are in any way required for one or more embodiments, or that one or more embodiments necessarily include these features, elements and/or states.

The teachings provided herein can be applied to other devices, systems, and methods, not necessarily explicitly described above. The elements and acts of the various embodiments described above can be combined to provide further embodiments.

While certain embodiments have been described, these embodiments have been presented by way of example only, and are not intended to limit the scope of the disclosure. Indeed, the novel methods, devices, and systems described herein may be embodied in a variety of other forms. Furthermore, various omissions, substitutions and changes in the form of the methods, devices, and systems described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the appended claims.

What is claimed is:

1. A monitoring device for monitoring a wrist of a user, the monitoring device comprising:
    a wrist strap configured to mount to a user's wrist, the wrist strap comprising a display positioned on a dorsal side of the user's wrist when the monitoring device is worn by the user;
    a main body attached to the wrist strap, the main body comprising:
        an emitter positioned to emit radiation through air toward a dorsal surface of the user's wrist when the monitoring device is worn by the user and the display is positioned on the dorsal side of the user's wrist;
        a sensor positioned to receive the radiation emitted by the emitter and primarily reflected by the dorsal surface of the user's wrist at least when the user's wrist is in extension and the monitoring device is worn by the user, and to output a signal in response to the received radiation reflected by the dorsal surface;
        a feedback module configured to provide immediate feedback to a user; and
        an integrated circuit configured to receive said signal and to control the feedback module to provide immediate feedback when the user's wrist enters an undesirable wrist position with respect to Carpal tunnel syndrome for a predetermined extended period of time, according to a degree of extension of the user's wrist as indicated by the signal.

2. The monitoring device of claim 1, further comprising a second emitter configured to emit radiation toward a dorsal surface of the user's wrist, the sensor also being configured to receive the radiation emitted by the second emitter and reflected by the dorsal surface of the user's wrist.

3. The monitoring device of claim 2, wherein the two emitters and sensor are substantially focused on the wrist of a user when worn by the user.

4. The monitoring device of claim 1, wherein the feedback module comprises one or more visual feedback modules configured to indicate to the user when the user's wrist enters an undesirable wrist extension with respect to Carpal tunnel syndrome.

5. The monitoring device of claim 1, wherein the monitoring device further comprises a data storage module configured to store data indicative of the degree of extension of the user's wrist over an extended period of time.

6. The monitoring device of claim 1, wherein the monitoring device also comprises a watch, the watch comprising a watch face on the dorsal side when worn by a user.

7. The monitoring device of claim 1, wherein the emitter emits infrared radiation.

8. A method of preventing and/or treating wrist and hand injury, the method comprising:
    emitting radiation through air toward a dorsal surface of a wrist of a user;
    receiving radiation primarily reflected from the dorsal surface of the wrist of the user;

estimating a degree of extension of the wrist according to the intensity of the reflected radiation received from the dorsal surface of the wrist of the user; and providing feedback to the user when the wrist is in an undesirable wrist extension with respect to Carpal tunnel syndrome for at least a predetermined extended period of time, according to the estimated degree of extension.

9. The method of claim 8, wherein the emitted radiation is infrared radiation.

10. The method of claim 8, further comprising estimating an angle of extension of the wrist.

11. The method of claim 8, further comprising indicating to the user when the wrist is in undesirable wrist extension with respect to Carpal tunnel syndrome.

12. The method of claim 8, further comprising calibrating the estimated degree of extension of the wrist by receiving radiation reflected from the wrist of the user as the user moves the wrist through a predetermined range of motion over a short time period.

13. The method of claim 8, further comprising transmitting data indicative of the estimated degree of extension to an auxiliary device.

14. The method of claim 8 further comprising transmitting data, indicative of a duration of undesirable extension with respect to Carpal tunnel syndrome, to an auxiliary device.

* * * * *